United States Patent [19]

Rathgeb

[11] 4,020,065
[45] Apr. 26, 1977

[54] 1,3,4-THIADIAZOLYL-(2)-HEXAHYDRO-TRIAZINONES

[75] Inventor: Paul Rathgeb, Basel, Switzerland

[73] Assignee: Ciba-Geigy Corporation, Ardsley, N.Y.

[22] Filed: Apr. 1, 1975

[21] Appl. No.: 564,017

[30] Foreign Application Priority Data

Apr. 3, 1974  Switzerland .................. 4689/74

[52] U.S. Cl. .................. 260/248 NS; 71/90; 260/247.1 M
[51] Int. Cl.² .................. C07D 251/08
[58] Field of Search .......... 260/248 NS, 247.5 C, 260/247.1 M; 71/90

[56] References Cited

UNITED STATES PATENTS

| 3,726,892 | 4/1973 | Cebalo | 71/90 X |
| 3,849,412 | 11/1974 | Krenzer | 260/248 NS |

FOREIGN PATENTS OR APPLICATIONS

| 70/08685 | 6/1971 | South Africa |
| 71/2599 | 10/1971 | South Africa |
| 966,283 | 8/1964 | United Kingdom |
| 1,340,267 | 12/1973 | United Kingdom |

OTHER PUBLICATIONS

Abstract of Belgian Patent 662,235, Publish 8/10/65, (Derwent Publication).

*Primary Examiner*—John M. Ford
*Attorney, Agent, or Firm*—Harry Falber

[57] ABSTRACT

New derivatives of 1,3,4-thiadiazolyl-(2)-hexahydro-triazinon of formula

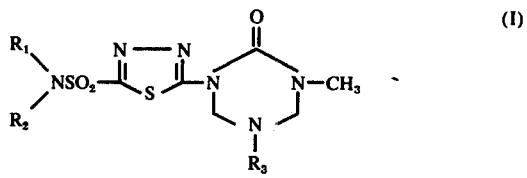

wherein
$R_1$ and $R_2$ are independently of each other $C_1$–$C_4$ alkyl or together with the nitrogen atom to which they are linked a pyrrolidino, piperidino or morpholino ring and
$R_3$ is an alkyl, alkenyl, alkinyl, alkoxyalkyl or alkylthioalkyl or the benzyl radical are disclosed and a process for the manufacture thereof. These compounds are herbicides and may be used for selective weed control in culture crops especially soya.

6 Claims, No Drawings

1,3,4-THIADIAZOLYL-(2)-HEXAHYDRO-TRIAZINONES

The present invention relates to new herbicidally effective 1,3,4-thiadiazolyl-(2)-hexahydrotriazinone derivatives, to processes for the production thereof, as well as to compositions and processes for selective weed control using these triazones as active substances.

The new 1,3,4-thiadiazolyl-(2)-hexahydrotriazinone derivatives correspond to formula I

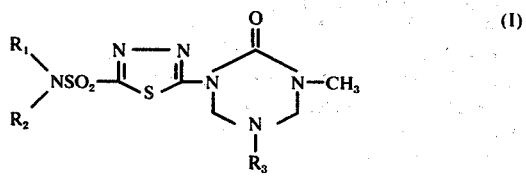

wherein
$R_1$ and $R_2$ each independently represent a $C_1$–$C_4$ alkyl radical, or together with the nitrogen atom carrying them the pyrrolidino, piperidino, hexahydroazepino or morpholino radical, and represents an alkyl, alkenyl, alkynyl, alkoxyalkyl or alkylthioalkyl radical, or the benzyl radical.

Alkyl radicals in formula I are preferably methyl, ethyl, n-propyl, isopropyl, n-butyl, isobutyl, sec.-butyl and tert.-butyl radicals. These radicals form also the alkyl moiety of alkoxyalkyl and alkylthioalkyl radicals. To be mentioned as alkenyl radicals are preferably the allyl and methallyl radical, and as alkynyl radicals preferably the propargyl radical.

The new 1,3,4-thiadiazolyl-(2)-hexahydrotriazinone derivatives of formula I are produced according to the present invention by a process in which a 1,3,4-thiadiazolyl-(2)-urea of formula II

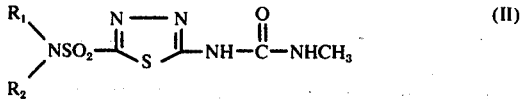

is cyclised with two equivalents of formaldehyde and one equivalent of an amine of formula III

$$R_3-NH_2 \quad (III).$$

In formulae II and III, the symbols $R_1$, $R_2$ and $R_3$ have the meanings given under formula I.

The described process is performed in the presence of solvents or diluents inert to the reactants, preferably in solvents miscible with water, such as alkanols, for example ethanol and isopropanol; also dioxane, tetrahydrofuran, dimethylformamide, etc., or water.

The reaction temperatures are between 0° and 150° C, preferably between 70° and 100° C.

The 1,3,4-thiadiazolyl-(2)-ureas of formula II used as starting materials are known: they are described in the British patent specification NO. 1,284,669.

The following example describes the production of the compounds according to the invention. Further triazinones of formula I obtained by this process are listed in the following table. Temperature values are given in degrees Centigrade.

EXAMPLE 16.8 g of a 40% aqueous methylamine solution is added within 5 minutes to a mixture of 53 g of N-[5-dimethylsulphamoyl-1,3,4-thiadiazolyl-(2)]-N'-methylurea, 38 g of 35% aqueous formaldehyde solution and 160 ml of ethanol. The temperature increases to about 45°. After the reaction has subsided, the mixture is refluxed for 30 minutes. The clear solution is concentrated in vacuo, the residue is stirred with 200 ml of ice water and the precipitated product is filtered off. After recrystallisation from ethanol/water 1:1, there is obtained 46 g of 1-[5'-dimethylsulphamoyl-1',-3',4'-thiadiazolyl-(2) ]-3,5-dimethyl-hexahydro-s-triazin-2-one having a melting point of 189°–190°. (This compound is designated in the following as Active Substance No. 1.)

| No. | Compound | Melting point |
|---|---|---|
| 2 | 1-[5'-Dimethylsulfamoyl-1',3',4'-thiadiazolyl-(2')]-3-methyl-5-allyl-hexahydro-s-triazin-2-one | 129° |
| 3 | 1-[5'-Pyrrolidinosulfonyl-1',3',4'-thiadiazolyl-(2')]-3-methyl-5-allyl-hexahydro-s-triazin-2-one | 132° |
| 4 | 1-[5'-Pyrrolidinosulfonyl-1',3',4'-thiadiazolyl-(2')]-3,5-dimethyl-hexahydro-s-triazin-2-one | 140°–141° |
| 5 | 1-[5'-Dimethylsulfamoyl-1',3',4'-thiadiazolyl(2')]-3-methyl-5-$\beta$-isopropylthioethyl-hexahydro-s-triazin-2-one | 132°–133° |
| 6 | 1-[5'-Pyrrolidinosulfonyl-1',3',4'-thiadiazolyl-(2')]-3-methyl-5-$\beta$-methylthioethyl-hexahydro-s-triazin-2-one | 78°–80° |
| 7 | 1-[5'-Dimethylsulfamoyl-1',3',4'-thiadiazolyl-(2')]-3-methyl-5-$\beta$-methylthioethyl-hexahydro-s-triazin-2-one | 128°–129° |
| 8 | 1-[5'-Pyrrolidinosulfonyl-1',3',4'-thiadiazolyl-(2')]-3-methyl-5-propargyl-hexahydro-s-triazin-2-one | 157°–158° |
| 9 | 1-[5'-Pyrrolidinosulfonyl-1',3',4'-thiadiazolyl-(2')]-3-methyl-5-$\beta$-ethyl-thioethyl-hexahydro-s-triazin-2-one | 86°–87° |
| 10 | 1-[5'-Dimethylsulfamoyl-1',3',4'-thiadiazolyl(2')]-3-methyl-5-$\beta$-ethyl-thioethyl-hexahydro-s-triazin-2-one | 84°–86° |
| 11 | 1-[5'-Pyrrolidinosulfonyl-1',3',4'-thiadiazolyl-(2')]-3-methyl-5-$\beta$-isopropylthioethyl-hexahydro-s-triazin-2-one | 107°–109° |
| 12 | 1-[5'-Dimethylsulfamoyl-1',3',4'-thiadiazolyl-(2')]-3-methyl-5-propargyl-hexahydro-s-triazin-2-one | 137°–138° |
| 13 | 1-[5'-Dimethylsulfamoyl-1',3',4'-thiadiazolyl-(2')]-3-methyl-5-$\gamma$-methoxypropyl-hexahydro-s-triazin-2-one | 81°–83° |
| 14 | 1-[5'-Diethylsulfamoyl-1',3',4'-thiadiazolyl-(2')]-3-methyl-5-tert-butyl-hexahydro-s-triazin-2-one | 109°–110° |
| 15 | 1-[5'-Diethylsulfamoyl-1',3',4'-thiadiazolyl-(2')]-3-methyl-5-isopropyl-hexahydro-s-triazin-2-one | 90°–91° |
| 16 | 1-[5'-(n-Butyl-methyl-sulfamoyl)-1',3',4'-thiadiazolyl(2')]-3,5-dimethyl-hexahydro-s-triazin-2-one | 98°–100° |
| 17 | 1-[5'-Diethylsulfamoyl-1',3',4'-thiadiazolyl-(2')]-3,5-dimethyl-hexahydro-s-triazin-2-one | 97°–99° |
| 18 | 1-[5'-Dimethylsulfamoyl-1',3',4'-thiadiazolyl-(2')]-3-methyl-5-isopropyl-hexahydro-s-triazin-2-one | 151°–153° |
| 19 | 1-[5'-Dimethylsulfamoyl-1',3',4'-thiadiazolyl-(2')]-3-methyl-5-n-butyl-hexahydro-s-triazin-2-one | 74°–75° |
| 20 | 1-[5'-Dimethylsulfamoyl-1',3',4'-thiadiazolyl-(2')]-3-methyl-5-tert-butyl-hexahydro-s-triazin-2-one | 158°–160° |
| 21 | 1-[5'-(Ethyl-methyl-sulfamoyl)-1',3',4'-thiadiazolyl-(2')]-3,5-dimethyl-hexahydro-s-triazin-2-one | |
| 22 | 1-[5'-Piperidinosulfonyl-1',3',4'-thiadiazolyl-(2')]-3,5-dimethyl-hexahydro-s-triazin-2-one | 117°–119° |
| 23 | 1-[5'-Morpholinosulfonyl-1',3',4'-thiadiazolyl-(2')]-3,5-dimethyl-hexahydro-s-triazin-2-one | 180°–182° |
| 24 | 1-[5'-Dimethylsulfamoyl-1',3',4'- | |

-continued

| No. | Compound | Melting point |
|---|---|---|
| | thiadiazolyl-(2')]-3-methyl-5-ethyl-hexahydro-s-triazin-2-one | |
| 25 | 1-[5'-Dimethylsulfamoyl-1',3',4'-thiadiazolyl-(2')]-3-methyl-5-n-propyl-hexahydro-s-triazin-2-one | |
| 26 | 1-[5'-Dimethylsulfamoyl-1',3',4'-thiadiazolyl-(2')]-3-methyl-5-n-hexyl-hexahydro-s-triazin-2-one | 84°–85° |
| 27 | 1-[5'-Dimethylsulfamoyl-1',3',4'-thiadiazolyl-(2')]-3-methyl-5-pyrrolidyl-hexahydro-s-triazin-2-one | 106°–107° |
| 28 | 1-[5'-Dimethylsulfamoyl-1',3',4'-thiadiazolyl-(2')]-3-methyl-5-benzyl-hexahydro-s-triazin-2-one | 135°–136° |
| 29 | 1-[5'-Morpholinsulfonyl-1',3',4'-thiadiazolyl-(2')]-3-methyl-5-n-butyl-hexahydro-s-triazin-2-one | 120°–122° |
| 30 | 1-[5'-Piperidinosulfonyl-1',3',4'-thiadiazolyl-3-methyl-5-n-butyl-hexahydro-s-triazin-2-one | 96°–97° |
| 31 | 1-[5'-Diethylsulfamoyl-1',3',4'-thiadiazolyl-(2')]-3-methyl-5-γ-methoxy-propyl-hexahydro-s-triazin-2-one | liquid |
| 32 | 1-[5'-Dimethylsulfamoyl-1',3',4'-thiadiazolyl-(2')-methyl-5-n-heptyl-hexahydro-s-triazin-2-one | 88°–89° |
| 33 | 1-[5'-Dimethylsulfamoyl-1',3',4'-thiadiazolyl-(2')]-3-methyl-5-sec.butyl-hexahydro-s-triazin-2-one | 77°–79° |

1,3,4-Thiadiazolyl derivatives having a similar structure and herbicidal properties have already been described in the German Pat. No. 1,249,003, in the Belgian Pat. No. 662,235, or in the South African Pat. No. 70/8685.

The active substances of formula I are new and possess excellent herbicidal properties, and are suitable for the control of gramineous and broad-leaved weeds in the widest variety of crops. Also annual and perennial species of weeds that are deep rooted and difficult to control are checked in growth or destroyed by these active substances. Thus, the new 1,3,4-thiadiazolyl-(2)-hexahydrotriazinones of formula I can be used in low concenrations for selective weed control in cereal, maize and cotton crops and in root crops and forage crops. In high concentrations, i.e. upwards of 5 kg of active substance per hectare, the new compounds can be used for the complete destruction and prevention of undesired plant growth. The triazinones of formula I can be applied both before germination (pre-emergence) and after germination (post-emergence) of the plants. They are particularly suitable for weed control in existing soya bean crops (glycine) and sweet potato crops (ipomoea patata).

Compounds of formula I that have proved especially suitable are those wherein $R_1$ and $R_2$ represent the methyl or ethyl radical, or together with the nitrogen atom carrying them a pyrrolidino, piperidino or morpholino radical. Particularly outstanding is the compound 1-[5'-dimethyl-sulphamoyl-1',3',4'-thiadiazolyl-(2')]-3,5-dimethyl-hexahydro-s-triazin-2-one.

The herbicidal action of the compounds of formula I is demonstrated by the following tests:

1. Herbicidal action with application of the active substances before germination of the plants (pre-emergence application).

Immediately before sowing of the test plants, the active substances are applied as aqueous suspensions, obtained from 25% wettable powders, to the surface of the soil. The seed trays are then kept in a greenhouse at 22°–23° with 50–70% relative humidity. Each active substance is applied in amounts corresponding respectively to 2 kg and 1 kg of active substance per hectare.

The following are used as test plants.

| Cultivated plants | Weeds |
|---|---|
| cotton, soya bean. | Lolium perenne, Digitaria sanguinalis, Setaria italica, Echinochloa crus galli, Amarantus retroflexus, Chrysanthemum leucanthemum, Galium aparine, Pastinaca sativa. |

The test results are evaluated after 14 days and 21 days. Evaluation is on the basis of a scale of values from 1–9:

1 = plants dead;
2–4 = intermediate stages of damage (over 50%—irreversible damage);
5–8 = intermediate stages of damage (below 50%—reversible damage);
9 = plants undamaged (control).

| pre-emergence Compound No. | 1 | 2 | 3 | 4 | 5 | 6 | 7 | 8 | 9 | 10 | 11 | 12 |
|---|---|---|---|---|---|---|---|---|---|---|---|---|
| Applied amount in kg/hectare | 2 1 | 2 1 | 2 1 | 2 1 | 2 1 | 2 1 | 2 1 | 2 1 | 2 1 | 2 1 | 2 1 | 2 1 |
| Plant | | | | | | | | | | | | |
| cotton | 8 8 | 7 8 | 7 9 | 9 9 | 9 9 | 8 9 | 8 8 | 7 7 | 8 8 | 8 9 | 8 8 | 7 8 |
| soya bean | 7 8 | 6 7 | 8 8 | 7 9 | 9 9 | 9 9 | 8 8 | 9 9 | 8 9 | 7 8 | 8 9 | 7 8 |
| lolium perenne | 2 3 | 1 3 | 2 4 | 2 4 | 1 2 | 3 7 | 1 2 | 2 7 | 1 6 | 1 3 | 2 7 | 2 4 |
| digitaria sang. | 1 1 | 1 1 | 1 1 | 1 2 | 2 2 | 2 2 | 1 1 | 1 1 | 2 3 | 1 1 | 1 1 | 1 1 |
| setaria italica | 1 1 | 1 1 | 1 1 | 1 1 | 1 1 | 1 3 | 1 1 | 1 1 | 1 2 | 1 1 | 1 2 | 1 1 |
| echinochloa crus g. | 1 1 | 1 1 | 1 1 | 1 1 | 1 1 | 1 1 | 1 1 | 1 1 | 1 2 | 1 1 | 1 1 | 1 1 |
| amaranthus retrofl. | 1 1 | 1 1 | 1 1 | 1 1 | 1 1 | 1 1 | 1 1 | 1 1 | 1 2 | 1 1 | 1 1 | 1 1 |
| chrysanth. leuc. | 1 1 | 1 1 | 1 1 | 1 1 | 1 1 | 1 2 | 1 1 | 1 1 | 1 2 | 1 1 | 2 2 | 1 1 |
| galium aparinae | 2 2 | 2 3 | 2 3 | 2 4 | 1 2 | 3 5 | 2 3 | 2 5 | 3 5 | 2 3 | 2 7 | 2 3 |
| pastinaca sativa | 2 2 | 1 2 | 2 4 | 2 4 | 1 7 | 3 6 | 1 6 | 2 8 | 2 8 | 1 7 | 3 5 | 4 5 |

2. Herbicidal action with application of the active substances after germination of the plants (post-emergence application)

The test plants are treated in the 2–4-leaf stage with aqueous suspensions of the active substances, obtained from 25% wettable powders. After the treatment, the plants are kept in a greenhouse at 22°–25° with 50°–70° relative humidity.

The following are used as test plants.

| Cultivated plants | Weeds |
|---|---|
| soya bean | Setaria italica |
| maize | Digitaria sanguinalis |
| cotton | Echinochloa crus galli |
| | Sesbania exaltata |
| | Amarantus retroflexus |
| | Sinapis alba |

The test results are evaluated after 19 days; the evaluation is made in the manner described under Test 1.

| post-emergence Compound No. | 1 | 2 | 3 | 4 | 5 | 6 | 7 |
|---|---|---|---|---|---|---|---|
| Applied amount kg/hectare | 2 1 | 2 1 | 2 1 | 2 1 | 2 1 | 2 1 | 2 1 |
| plant | | | | | | | |
| cotton | 8 8 | 7 8 | 9 9 | 7 8 | 3 7 | 5 7 | 5 7 |
| soya bean | 7 8 | 7 7 | 9 9 | 9 9 | 8 9 | 7 8 | 7 8 |
| maize | 7 7 | 5 7 | 9 9 | 9 9 | 5 8 | 7 9 | 6 7 |
| setaria italica | 1 1 | 1 1 | 3 3 | 3 6 | 3 3 | 1 3 | 1 1 |
| digitaria sang. | 1 1 | 1 1 | 2 3 | 2 2 | 1 4 | 1 4 | 1 1 |
| echinochloa crus g. | 1 1 | 1 1 | 3 3 | 2 2 | 1 2 | 2 4 | 1 1 |
| sesbania exaltata | 1 1 | 1 4 | 2 3 | 9 9 | 3 5 | 4 4 | 4 3 |
| amarantus retrofl. | 1 2 | 2 2 | 3 4 | 2 3 | 2 3 | 3 4 | 1 2 |
| sinapis alba | 1 1 | 1 1 | 2 2 | 1 2 | 1 2 | 1 3 | 1 1 |

The compositions according to the invention are produced in a manner known per se by the intimate mixing and/or grinding of active substances of the general formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;

water-dispersible active-substance concentrates: wettable powders, pastes and emulsions;

liquid preparations: solutions.

The solid preparations (dusts, scattering agents and granulates) are produced by the mixing to the active substances with solid carriers. Suitable carriers are, e.g., kaolin, talcum, bole, loess, chalk, limestone, ground limestone, attapulgite, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to approx. 0.1 mm; for scattering agents approx. 0.075 to 0.2 mm; and for granulates 0.2 mm or coarser.

The concentration of active substance in the solid preparations is 0.5 to 80%.

It is possible to add to these mixtures also additives stabilising the active substance, and/or nonionic, anionactive and cation-active substances which improve, e.g., the adhesiveness of the active substances on plants and parts of plants (adhesives and agglutinants), and/or ensure better wettability (wetting agents) as well as dispersibility (dispersing agents). Suitable adhesives are, for example, olein/lime mixture, cellulose derivatives (methyl cellulose, carboxymethyl cellulose), hydroxyethylene glycol ethers or monoalkyl and dialkyl phenols having 5 to 15 ethylene oxide radicals per molecule and 8 to 9 carbon atoms in the alkyl radical, lignin-sulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances, and anti-foaming agents and, optionally, solvents. The concentration of active substance in these preparations is 5–80%.

The wettable powders and pastes are obtained by the mixing and grinding of the active substances with dispersng agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N-dialkylated amides, N-oxides of amines, especially trialkylamines, and mineral oil fractions boiling in the range of 120° to 350° C. The solvents must be practically odourless, nonphytotoxic, inert to the active substances and not readily combustible.

Furthermore, the agents according to the invention can be used in the form of solutions. For this purpose, the active substance, or several active substances, of the general formula I is dissolved in suitable organic solvents, solvent mixtures, water, or mixtures of organic solvents with water. As organic solvents, it is possible to use aliphatic and aromatic hydrocarbons, their chlorinated derivatives. alkylnaphthalenes, mineral oils on their own or in admixture with each other. The solutions should contain the active substances in a concentration of 1 to 20%.

These solutions can be applied either by means of a propellent gas (as spray), or by means of special sprayers (as aerosol).

Other biocidal active substances or agents can be mixed with the described compositions of the invention. For the broadening of their sphere of action, the new compositions can for example contain, in addition to the stated compounds of the general formula I, insecticides, fungicides, bactericides, fungistatics, bacteriostatics or nematocides. The compositions of the invention may also contain fertilisers, trace elements, etc..

Preparations of the new active substances of the general formula I are described in the following. Parts are given as parts by weight.

Granulate

The following substances are used to produce a 5% granulate:
5 parts of Active Substance No. 1,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The solution obtained is sprayed onto kaolin, and the acetone is subsequently evaporated off in vacuo.

Wettable Powders

The following constituents are used to prepare (a) a 40%, (b) and (c) a 25%, and (d) a 10% wettable powder:
a. 40 parts of Active Substance No. 2,
 5 parts of sodium lignin sulphonate,
 1 part of sodium dibutyl-naphthalene sulphonate,
 54 parts of silicic acid;
b. 25 parts of Active Substance No. 1,
 4.5 parts of calcium lignin sulphonate,
 1.9 parts of Champagne chalk/hydroxyethyl cellulose mixture (1:1),
 1.5 parts of sodium dibutyl naphthalene sulphonate,
 19.5 parts of silicic acid,
 19.5 parts of Champagne chalk, 28.1 parts of kaolin;
c. 25 parts of Active Substance No. 7,
 2.5 parts of isooctylphenoxy-polyoxyethyleneethanol,
 1.7 parts of Champagne chalk/hydroxyethyl cellulose mixture (1:1),
 8.3 parts of sodium aluminium silicate,
 16.5 parts of kieselguhr,
 46 parts of kaolin;
d. 10 parts of Active Substance No. 1,
 3 parts of a mixture of the sodium salts of saturated fatty alcohol sulphates,
 5 parts of naphthalenesulphonic acid/formaldehyde condensate,
 82 parts of kaolin.

The active substances are intimately mixed, in suitable mixers, with the additives, and the mixture is ground on the appropriate mills and rollers. There are obtained wettable powders that can be diluted with water to give suspensions of any desired concentration.

Emulsifiable Concentrates

The following substances are used to produce (a) a 10% and (b) a 25% emulsifiable concentrate:
a. 10 parts of Active Substance No. 2,
 3.4 parts of epoxidised vegetable oil,
 3.4 parts of a combination emulsifier consisting of fatty alcohol polyglycol ether and alkylarylsulphonate calcium salt,
 40 parts of dimethylformamide,
 43.2 parts of xylene;
b. 25 parts of Active Substance No. 1,
 2.5 parts of epoxidised vegetable oil,
 10 parts of an alkylarylsulphonate/fatty alcohol-polyglycol ether mixture,
 5 parts of dimethylformamide,
 57.5 parts of xylene.

From these concentrations it is possible to obtain, by dilution with water, emulsions of any desired concentration.

I claim:
1. A 1,3,4-thiadiazolyl-(2)-hexahydrotriazinone compound of the formula

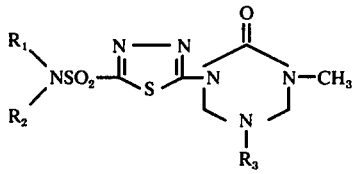

wherein
R$_1$ and R$_2$ each independently represent C$_1$–C$_4$ alkyl, or together with the nitrogen atom carrying them the pyrrolidino, piperidino, hexahydroazepino or morpholino radical, and
R$_3$ represents C$_1$–C$_7$ alkyl, C$_3$–C$_4$ alkenyl, C$_3$ alkynyl, alkoxyalkyl having C$_1$–C$_4$ alkyls or alkylthioalkyl having C$_1$–C$_4$ alkyls, or benzyl.

2. The compound of claim 1, wherein R$_1$ and R$_2$ each independently represent methyl or, ethyl or together with the nitrogen atom carrying them the pyrrolidino, piperidino or morpholino radical.

3. 1-[5'-Dimethylsulphamoyl-1',3',4'-thiadiazolyl-(2')]-3,5-dimethyl-hexahydro-s-triazin-2-one.

4. 1-[5'-Dimethylsulphamoyl-1',3',4'-thiadiazolyl-(2')]-3-methyl-5-β-ethylthioethyl-hexahydro-s-triazin-2-one.

5. 1-[5'-Pyrrolidinosulphonyl-1',3',4'-thiadiazolyl-(2')]-3-methyl-5-β-methylthioethyl-hexahydro-s-triazin-2-one.

6. 1-[5'-pyrrolidinosulphonyl-1',3',4'-thiadiazolyl-(2')]-3-methyl-5-allyl-hexahydro-s-triazin-2-one.

* * * * *